United States Patent [19]
Reddy et al.

[11] Patent Number: 5,981,191
[45] Date of Patent: Nov. 9, 1999

[54] PROCESS FOR IDENTIFYING MUTAGENS AND ANTIMUTAGENS

[75] Inventors: Manjula Reddy; Jayaraman Gowrishankar; Shanti M. Bharatan, all of Hyderabad, India

[73] Assignee: Council of Scientific & Industrial Research, India

[21] Appl. No.: 09/175,073

[22] Filed: Oct. 19, 1998

[51] Int. Cl.$^6$ ...................................................... C12Q 1/68

[52] U.S. Cl. ................................................ 435/6; 435/440

[58] Field of Search ........................................ 435/6, 440

[56] References Cited

PUBLICATIONS

Skaliter et al., *Mutation Research*, vol. 267, 1992, pp. 139–151.

*Primary Examiner*—James Ketter
*Attorney, Agent, or Firm*—Fish & Richardson P.C.

[57] ABSTRACT

The invention relates to a process for determining the frequency of mutations in living and essentially nondividing cells; a process for obtaining strains of a particular specified genotype in which such mutation frequencies may be determined; and a process for determining the effects of various agents including chemical substances and genes on the frequency of mutations in living and essentially nondividing cells.

16 Claims, No Drawings

PROCESS FOR IDENTIFYING MUTAGENS AND ANTIMUTAGENS

BACKGROUND OF THE INVENTION

This invention is in the general field of testing for mutagenic activity.

Non-natural substances or compositions are often tested for their mutagenic potential because of the high correlation between mutagenic activity and carcinogenic activity. Furthermore, there is also the expectation that compounds with antimutagenic activity would be beneficial in the prevention of cancers. Several methods and assays have therefore been developed to determine the mutagenic or antimutagenic activity of substances in bacteria, yeast, animal cell cultures and whole animals. For example, the Ames test or variants thereof is widely used as a test of bacterial mutagenicity [Ames et al. (1973) Proc. Natl. Acad. Sci. USA 70:782–786; McCann et al. (1975) Proc. Natl. Acad. Sci. USA 72:5135–5139; Maron and Ames (1983) Mutat. Res. 113:173–215].

In the past few years, it has been recognized that mutations can arise not only in dividing cells in the course of replication of the genetic material or in the course of repair following to the genetic material, but that they can also arise in populations of essentially nondividing cells. There is also evidence that the mechanism by which mutations arise in nondividing cells are different from those in dividing cells [reviewed in Foster (1993) Annu. Rev. Microbiol., 47:467–504; Rosenberg et al. (1995) Mol. Microbiol. 18:185–189].

SUMMARY OF THE INVENTION

We have discovered a novel conditional lethal genetic strategy that is designed to determine the frequency of occurrence of at least one particular target mutation arising in a population of living and essentially non-dividing cells.

Accordingly, one aspect of the invention features a method for determining the frequency with which at least one target mutation arises in a population of living and essentially nondividing cells, including subjecting a population of cells having indicator DNA to a stationary phase of growth such that a mutation arising within the indicator DNA confers a detectable phenotype. The frequency of occurrence of a particular target mutation is determined by comparing the number of cells that undergo a phenotypic change to the total number of cells within the stationary phase population.

In another aspect the invention features a method for determining the frequency with which at least one target mutation arises in a population of living and essentially non-dividing cells, the method includes the steps: (a) subjecting a cell population comprising indicator DNA, which produces a detectable phenotype when mutated, to growth conditions, wherein the growth conditions are mutant-lethal resulting in a mutant-free cell population; (b) subjecting said resulting cell population to resting conditions which induce a cell cycle stationary phase; (c) shifting said mutant-lethal condition to a mutant-tolerant condition under which mutants are now viable (d) detecting the phenotype in said viable mutant cells and determining the frequency of occurrence of the particular mutation in the cell population by comparing the number of cells that undergo a phenotypic change to the total number of cells within that cell population. The indicator DNA can be any DNA sequence that can confer a detectable phenotype when mutated.

In another embodiment of the invention, the method includes a cell population that has conditionally-lethal DNA. The conditionally-lethal DNA can be used to eliminate those cells in which a target mutation in the indicator DNA arises. The presence of the conditionally-lethal DNA ensures that during growth, the cell population is free of cells bearing the target mutation. The mutant-free cell population can then be subjected to "stationary phase", a phase where the cells are living and essentially non-dividing. Upon reaching this phase the conditions are altered such that the conditionally lethal DNA permits growth of mutant cells which bear the target mutation. The conditionally-lethal DNA in a cell population can include a temperature sensitive galE mutation or a temperature sensitive kanamycin-resistance gene, or both.

Another embodiment of the invention provides a method for determining the effect of a potential mutagen on the frequency with which a target mutation occurs within a resting and essentially non-dividing cell population. The potential mutagen can be any substance or agent, e.g., a chemical compound. The mutagen can be a chemical toxin (e.g., arsenic), an environmental mutagen, or an environmental carcinogen (e.g., a heterocyclic amine (HCA) such as 2-amino-1-methyl-6-phenylimidazo[4,5-b]pyridine (PhIP)). Potential mutagens include but are not limited to: particulate organics from urban air; municipal waste incinerator emissions; cigarette smoke; organic extracts of chlorinated drinking water; inorganic acid mists, insecticides (e,g, epichlorohydrin); metals (e.g,. cadmium); sunlight or UV-radiation). In another embodiment, the potential mutagen is a drug or a combination of drugs that is/are used to treat a particular disease, e.g., methylating agents; alkylating agents (e.g., cyclophosphamide and ifosfamide); platanium compounds (e.g., cisplatin and carboplatin); or other cytotoxic agents (e.g., azathioprine, chlorambucil, and methotrexate). The potential mutagen can be introduced at one or more of steps (a) through (c). Preferably the mutagen is added in step (c).

In another embodiment, the invention features a method for determining the effect of a potential antimutagen on the frequency with which a target mutation occurs within a resting and essentially non-dividing cell population. The potential antimutagen can be introduced at one or more of steps (a) through (c). Preferably the antimutagen is added in step (c).

In another embodiment, the invention features a method for determining the combined effect of both a potential mutagen and a potential antimutagen on the frequency with which a target mutation occurs within a resting and essentially non-dividing cell population. The combined potential mutagen and potential antimutagen can be introduced at one or more of steps (a) through (c). Preferably the combination is added in step (c).

In general, "the population of cells" can be any cell type including, but not limited, to populations of eukaryotic or bacterial cells. Preferably the cells are bacterial cells, e.g., *Escherichia coli*.

In another embodiment of the invention features an indicator DNA sequence that encodes a detectable protein.

In still another embodiment of the invention, the invention features an indicator DNA sequence that only expresses a detectable protein in response to an inducer substance. Preferably the detectable protein is β-galactosidase and the inducer is isopropyl β-thiogalactopyranoside. In this embodiment, target mutations arising within the indicator DNA are those which affect expression such that the indicator DNA is now constitutively expressed and no longer requires the inducer substance to produce the detectable protein.

In yet another embodiment, the indicator DNA in a cell population contains a mutation (e.g., a point mutation), such that the cells are unable to express a detectable protein of interest (i.e., a protein whose activity can be detected). In this embodiment, target mutations arising within the indicator DNA permit expression of the indicator DNA and allow the subsequent production of the detectable protein of interest.

In still yet another embodiment, the indicator DNA in a cell population contains a mutation (e.g., a point mutation), that renders the cells incapable of producing a functional protein of interest. In this embodiment, target mutations arising within the indicator DNA permit expression of a functional, and now detectable, protein of interest.

In another aspect of the invention, the invention features bacterial cells which have been genetically engineered to suit the above described novel method. Examples of these bacterial cells include the *Escherichia coli* strains GJ2219, GJ2406, GJ1823 or GJ1885.

In another embodiment of the invention, the invention features a method for determining the frequency of excision of an insertion encoding kanamycin (Kan)-resistance in a population of living and essentially nondividing *Escherichia coli* cells. As a condition necessary for the practice of this embodiment of the invention, a process is also described for obtaining a temperature-sensitive mutation in a gene encoding Kan-resistance (conditionally-lethal DNA) in *Escherichia coli*, and for constructing strains of *Escherichia coli* that carry both a temperature-sensitive Kan-resistance mutation as well as a second Kan-resistance insertion in a suitable target locus such as the lacZ gene (indicator DNA).

According to another embodiment of this invention, a method is described that determines the frequency of occurrence in living and essentially nondividing *Escherichia coli* cells of a set of target mutations that is comprised of nucleotide base changes that convert a parental cell essentially incapable of synthesizing functional-β-galactosidase into a mutant that is capable of synthesizing functional β-galactosidase. As a condition necessary for the practice of this embodiment of the invention, a process is also described for obtaining a temperature-sensitive mutation in the *Escherichia coli* galE gene (conditionally-lethal DNA), and for constructing strains of *Escherichia coli* that carry both a temperature-sensitive galE mutation as well as a mutation in the lacZ gene (indicator DNA) that confers a lactose fermentation-negative phenotype. According to this embodiment, any of a variety of different lacZ mutations may be employed whose frequency of reversion or pseudo-reversion to Lac$^+$ in living and essentially nondividing cells may be determined.

According to yet another embodiment of this invention, a method is described which determines the frequency of occurrence in living and essentially nondividing *Escherichia coli* cells of a set of target mutations that is comprised of nucleotide base changes that converts a parental cell which is capable of synthesizing functional β-gelactosidase in the presence of an inducer such as isopropyl β-D-thiogalactopyranoside (IPTG) but which is incapable of synthesizing functional β-gelactosidase in the absence of such an inducer, into a mutant which is capable of substantial constitutive synthesis of functional β-gelactosidase even in the absence of the inducer. As a condition necessary for the practice of this embodiment of the invention, a process is also described for obtaining a temperature-sensitive mutation (conditionally-lethal DNA) in the *Escherichia coli* galE gene, and for constructing strains of *Escherichia coli* that carry both a temperature-sensitive galE mutation as well as a lac locus (indicator DNA) of a particular specified genotype. This embodiment provides a method for determining the frequency of forward mutations in the lacI repressor gene within a population of living and essentially nondividing bacterial cells. A particular advantage of this embodiment is that, unlike reversion analysis, the ensemble of molecular events which comprise the said set of the said forward mutations in the lacI gene represent an extremely wide mutational spectrum.

As used herein, "indicator DNA" means a DNA sequence that when mutated in a stationary phase cell confers a detectable phenotype. The mutation can arise in regulatory DNA (e.g., promoter DNA), or can arise within the gene itself (e.g., a point mutation in the coding region of a gene). The presence of the mutation in the indicator DNA affects the transcription, and/or translation, or function of a particular gene product such that a detectable phenotypic change results. Any known sequence whose gene product has a detectable phenotype can be used as the indicator DNA, e.g., the lacZ gene which encodes B-galactosidase.

As used herein "conditionally-lethal DNA" refers to a DNA sequence that can be used under a certain condition to eliminate cells in which target mutations arise during cell growth. Such a DNA sequence can be used to ensure that upon reaching stationary phase a cell population does not contain any target mutations. Examples of conditionally-lethal DNA include a temperature-sensitive kanamycin gene and a temperature-sensitive GalE gene.

As used herein "living and essentially non-dividing cells" refers to cells which are in a stationary phase of growth, i.e., when there is neither an increase in cell number or cell constituents.

As used herein "target mutations" refer to an alteration in sequence in the indicator DNA such that the indicator DNA produces a detectable change in phenotype in said living and non-dividing cells.

Unless otherwise defined, all technical and scientific terms used herein have the same meaning as commonly understood by one of ordinary skill in the art to which this invention belongs. In case of conflict, the present application, including definitions, will control. All publications, patents, and other references mentioned herein are incorporated by reference.

Although methods and materials similar or equivalent to those described herein can be used in the practice or testing of the present invention, the preferred methods and materials are described below. The materials, methods, and examples are illustrative only and are not intended to be limiting. Other features and advantages of the invention will be apparent from the detailed description, and from the claims.

DETAILED DESCRIPTION OF THE INVENTION

Since the human body is comprised of large numbers of predominantly nondividing cells, it is quite possible and indeed likely that at least some cancers have their origins as mutations in such nondividing cells. The identification of agents that may increase or decrease the frequency of occurrence of such mutations therefore becomes an important issue.

However, none of the currently employed techniques for mutagenicity testing address the question, specifically and exclusively, of determination of mutation frequencies in predominantly nondividing cells. The problem in particular is that any individual mutational change can occur in both a dividing cell during the course of replication of the genetic material as also in a nondividing cell, so that it is often not feasible to determine whether any individual mutant in a population arose during cell division or in the stationary phase.

Accordingly this invention features a novel conditional lethal genetic strategy by which a parental population of cells is able to survive and grow under both restrictive and permissive conditions whereas mutants of a particular class arising in that population are killed under the former condition and survive under the latter. Thus, if the parental population is grown to stationary phase with exposure to the restrictive condition, all mutants of the said class that arose during the phase of exponential growth will be killed. If the population is then shifted to the permissive condition, the only mutants of the said class that would survive and be scored are those which arose after shift to the latter condition, that is, those which arose within the population of essentially nondividing cells.

The said novel conditional lethal genetic strategy requires the development of strains or cell lines with an unusual phenotypic property. Unlike ordinary conditional lethal strategies in which the conditional lethal phenotype applies to all cells in a population, the strategy disclosed in the present invention is one in which the conditional lethal phenotype applies only to those rare cells within the population in which mutations of a particular class have occurred. The remaining vast majority of cells in the population can in fact survive and grow under both the restrictive and permissive conditions.

According to this invention, there is provided a process based upon the said novel genetic strategy for determining the frequency of occurrence of a set of target mutations in a population of living and essentially nondividing cells, said process being comprised of first obtaining the said population by growth from a smaller inoculum of cells with the said population being either simultaneously or consequently subjected to a condition in which mutants bearing any mutation belonging to the said set, that had arisen during the said growth, are killed, and then shifting the said population to another condition in which mutants bearing any mutation belonging to the said set retain viability.

Indicator DNA

The indicator DNA is a DNA sequence that when mutated in a stationary phase cell confers a readily storable phenotype. The choice of an appropriate indicator DNA is influenced in part by the type of cell population being examined. For example, if the cell is a bacterial cell the indicator DNA is likely to be of bacterial origin whereas if the cell is a eukaryotic cell the indicator DNA can be of bacterial or eukaryotic origin. Those skilled in the art will be able to choose an indicator DNA appropriate for the cell type under examination.

The indicator DNA can be any DNA sequence that confers upon a cell a detectable phenotype. The indicator DNA can be of any origin synthetic or natural. Examples of indicator DNA include, but are not limited to, the following: lacZ, TnphoA, the chloramphenicol acetyl transferase gene, the green fluorescent protein gene, and the firefly luciferase gene. Furthermore, the indicator DNA need not necessarily be wild type with respect to DNA sequence. In some instances it may be more preferable to use mutant versions of a gene or DNA sequence that constitutes the indicator DNA (e.g., a mutant form of lacZ that results in the production of a non-functional form of b-galactosidase).

Methods for producing mutant versions of the indicator DNA sequence are known in the art, e.g., site-directed mutagenesis. Alterations in the natural sequence can be due to an excision mutation which results from the excision of one or more nucleotide from the indicator DNA sequence. Alterations in the natural sequence can also result from insertion mutations which are generated by inserting one or more nucleotide bases into the indicator DNA sequence.

Mutations in the indicator DNA sequence can include forward mutations, reverse mutations or regulatory mutations. A forward mutation refers to a mutation arising in the indicator DNA whereby the indicator DNA sequence which normally does not produce a detectable protein undergoes an alteration in sequence such that the indicator DNA sequence can now consitutively produce a detectable protein.

A reverse mutation refers to an alteration in the genetic sequence of the indicator DNA that results in restoration of the wild type phenotype.

A regulatory mutation refers to a mutation that occurs within the regulatory sequence of the indicator DNA such that the normal regulatory sequences that control expression of the detectable protein are altered.

Conditionally Lethal DNA

The conditionally-lethal DNA refers to a DNA sequence that can be used under a certain condition to eliminate cells in which target mutations arise during cell growth. The conditionally-lethal DNA should be compatible with the condition the experimenter wishes to use in order to shift cells from a mutant-lethal environment to a mutant-tolerant environment. For example, if the shift from a mutant-lethal to a mutant-tolerant growth condition is to be controlled by a change in temperature then a particular temperature-sensitive mutant allele may be used as the conditionally-lethal DNA.

Shift from a Restrictive to a Permissive

The novel genetic strategy may employ any of a variety of means that satisfy the condition of shift from a restrictive to a permissive growth condition for the mutant cells, including but not limited to shift from high temperature to low temperature; shift from low temperature to high temperature; shift from a medium of high water activity (ionic strength) to one of low water activity; shift from medium of low water activity to one of high water activity; or shift from medium containing a growth-inhibiting compound for the mutant cells to one that does not contain the growth-inhibiting compound, for example, by addition to the medium of a substance that degrades or otherwise reduces the activity of the growth-inhibiting compound. A preferred aspect of the invention is to employ a shift in the incubation temperature to achieve a transfer from restrictive to permissive growth conditions for the mutant cells. A further preferred aspect of the invention is to employ a shift from a higher to a lower incubation temperature for this purpose.

According to the invention, the period of exposure to the restrictive condition, to enable killing of mutant cells that arise during the exponential growth phase of the parental population, may either be partially or completely overlapping with, or be subsequent, that of exponential growth of the parental population.

The present invention may be practiced by employing either addition to the culture medium, or removal from the culture medium, of particular agents in order to achieve the shift from the restrictive to the permissive condition. Alternatively, the shift from the restrictive to the permissive condition may be achieved without overt alteration of the chemical composition of the culture medium. A preferred aspect of this invention is to achieve the shift from the restrictive to the permissive condition by alteration of some particular parameter, as exemplified by but not limited to the temperature of incubation, which does not involve overt manipulation of the composition of the culture medium.

Detection of Mutant Phenotype

The said process based upon the said novel genetic strategy may be applied to cultures of cells grown either as suspensions in liquid medium; or as layers, or lawns, or colonies, within or on gels or solid surfaces, with consequent restricted diffusional mobility of individual cells. A preferred aspect of this invention is to adopt conditions in which the descendants of a mutant cell, said mutant cell having arisen within a population of parental cells by a mutation belonging to a specified target class, remain clustered together in the culture medium so as to form a discrete clone. One advantage of such a method is that individual and independent mutational events can each be conveniently scored as a discrete cluster of the mutant cells. Examples of such mutant clusters include but are not limited to cells which adopt a color change; papillae on the surface of a bacterial lawn or colony; or transformed foci of mammalian cells in either soft agar or monolayer cultures.

Addition of Mutagen and/or Antimutagen

Determining the effect of a substance or mixture of substances on the frequency of occurrence of a set of target mutations in a population of living and essentially nondividing cells includes:

a. developing an assay as described above for determining the frequency of occurrence of the said set of target mutations in the said population; and b. performing the said assay in the presence of the said substance or mixture of substances.

The potential mutagen can be any substance or agent, e.g., a chemical compound. The mutagen can be a chemical toxin (e.g., arsenic), an environmental mutagen, or an environmental carcinogen (e.g., a heterocyclic amine (HCA) such as 2-amino-1-methyl-6-phenylimidazo[4,5-b]pyridine (PhIP)). Potential mutagens include but are not limited to: particulate organics from urban air; municipal waste incinerator emissions; cigarette smoke; organic extracts of chlorinated drinking water; inorganic acid mists, insecticides (e,g, epichlorohydrin); metals (e.g,. cadmium); sunlight or UV-radiation). In another embodiment, the potential mutagen is a drug or a combination of drugs that is/are used to treat a particular disease, e.g., methylating agents; alkylating agents (e.g., cyclophosphamide and ifosfamide); platanium compounds (e.g., cisplatin and carboplatin); or other cytotoxic agents (e.g., azathioprine, chlorambucil, and methotrexate). The potential mutagen can be introduced at one or more of steps (a) through (c). Preferably the mutagen is added in step (c).

In the examples below, we provide a detailed description of the preferred embodiments of the invention. The examples are only illustrative, and the practice of the invention is not limited to or by these examples. It is to be expected that additional configurations of the same invention may be achieved by modifications that involve materials and processes that are already known in the art.

EXAMPLES

1. The genotypes of *Excherichia coli* strains used in the examples are listed in the Table below.

| Strain | Genotype |
|--------|----------|
| MC4100 | F− Δ (argF-lac)U169 rpsL150 relA1 araD139 flbB5301deoCI ptsF25 |

-continued

| Strain | Genotype |
|--------|----------|
| MG1655 | F− rph-1 |
| CAG18420 | F− rph-1 lacZU118 lacI3098::Tn10Kan |
| CSH100 | ara Δ (gpt-lac) 5/F' [pro A+B+ lacI$^q$ lacPL8] |
| CSH142 | ara Δ (gpt-lac) 5 |
| CSH143 | ara Δ (gpt-lac) 5 gyrA/F [pro+B+ lacI lacZ (Am)] |
| KL226 | HfrC (P02A) tonA22 ompF relA pit-10 T2$^r$ |
| NR3835 | ara Δ (gpt-lac) 5 thi trpE997/F [proA+B+ lacI$^q$ lacPL8] |
| PL-2 | HfrH (PO1) thi-1 relA1 galE28 spoT1 |
| GJ513 | Hfr (PO45) thi-1 relA1 spoT1 lacZ4525::Tn10dKan |
| GJ523 | MC4100 proU224::lac(λ) zfi-900::Tn10 zbh-900::Tn10dKan |
| GJ1000 | MC4100 [φ80d supF (Ts)] |
| GJ1112 | GJ1000 zbh-900::Tn10dKan (Ts)1 |
| GJ1823 | MG1655 zbh-900::Tn10dKan (Ts) 1 lacZ4525::Tn10dKan |
| GJ1885 | ara zbh-900::Tn10dKan (Ts) 1 lacZ4525:;Tn103Kan |
| GJ2202 | CSH143 galE28 zbh-900::Tn10dKan (Ts)1 |
| GJ2203 | GJ2202 galE516 (Ts) |
| GJ2218 | CSH142 galE516 (Ts) zbh-900::Tn10dKan (Ts) 1 galP-528 mgl-353 |
| GJ2219 | ara galE516 (Ts) zbh-900::Tn10dKan (Ts) 1 galP528 mgl-353 |
| GJ2220 | GJ2219 lacZ4525::Tn10dKan |
| GJ2231 | GJ1885 recA56 srl::Tn10/F$^1$ [pro A+B+ lacI$^q$ lacPL8 zah910::Tn10dCm |
| GJ2251 | GJ1885 recA56srl::Tn10/F' [A+B+ lacI$^q$ lacPL8 zah910::Tn10d Cm] |
| GJ2406 | GJ2219 lacI$^q$ lacPL8 zah910::Tn10dCm |
| GJ2253 | GJ2219 lacZ4525::Tn10dKan |
| GJ2254 | GJ2219 lacI$^q$ lacPL8 zah910::Tn10dCm |

Strains MG1655 and PL-2 were obtained from the Coli Genetic Stock Center, Department of Biology, Yale University, P.O. Box 6666, New Haven, Conn. 06511-74444, USA. Strains CSH100, CSH142 and CSH143 were purchased from Dr J. H. Miller, Department of Microbiology and Molecular Genetics, College of Letters and Science, 5304 Life Sciences building, 405 Hilgard Avenue, Los Angeles, Calif. 90024-1489, USA as part of the Cold Spring Harbor strain kit. Strain CAG18420 was obtained as part of the mapping strain kit from Prof Carol Gross at Dept. of Bacteriology, University of Wisconsin, Madison, Wis. 53706, USA and is also available from Coli Genetic Stock Center. Strain NR3835 was obtained from the laboratory of Dr M. Radman, Laboratoire de Mutagenese, Institute Jacques Monod, Centre National de la Recherche Scientifique, UMR 9922, 2 Place Jessieu, 75251 Paris Cedex 05, France.

2. Plasmid pAA102 was obtained from Dr. S. J. W> Busby, School of Biochemistry, University of Birmingham, Edgbaston, Birmingham B15 2TT, UK.

3. Bacteriophage P1 was obtained from Prof. A. J. Pittard, Dept. of Microbiology, University of Melbourne, Parkville, VIC 3052, Australia. Lambda bacteriophage NK 1324, which carries the Tn10-derived transposable element Tn10dCm, was obtained from Dr Kleckner, Department of Biochemistry and Molecular Biology, Harvard University, Cambridge, Mass. 02138, USA 4. Bacteriological media materials were purchased from Difco Laboratories (P.O. Box 331058, Detroit, Mich. 48232-7058, USA). Antibiotics and fine chemicals were purchased from Sigma (P.O. Box 14508, St. Louis, Mo. 63178, USA). Restriction endonucleases and enzymes used during DNA cloning were obtained from New England Biolabs (32 Tozer Road, Beverly, Mass. 01915-5599, USA).

5. Nutrient and minimal growth media were derived, respectively, from LB and minimal A media described in A Short Course in Bacterial Genetics: A Laboratory Manual and Handbook for *Escherichia coli* and Related Bacteria J.

H. Miller (1992), Cold Spring Harbor Laboratory Press, Cold Spring Harbor, N.Y., USA.

Procedures for P1 transduction, replica plating, conjugation and transposition of Tn10-derived elements from Lambda phage were also performed as described in the reference of Miller cited above. Solid media were prepared with the addition of 2% Difco Bacto agar. When used, antibiotics were added at the following final concentrations (micrograms per ml); ampicillin (Amp), 100; tetracycline (Tet), 15; kanamycin (Kan), 50; and chloramphenicol (Cm), 25. Unless otherwise indicated, D-glucose, D-lactose, D-galactose, Casamino acids, IPTG, Phenyl β-D-galactoside (PG) and 5-bromo 4-chloro 3-indolyl β-D-galactopyranoside (Xgal) were used at final concentrations, respectively, of 0.2%, 0.2%, 0.2%, 0.5%, 1 mM, 0.05%, and 40 micrograms per ml. L-Amino acid supplements were added when required at a final concentration each of 40 micrograms per ml. The routine maintenance and growth of strains carrying the galE516 (Ts) mutation were done at 30° C. in LB medium supplemented with 0.2% glucose. Unless otherwise indicated, cultures were incubated aerobically and at 37° C.

6. Unless mentioned otherwise, the preparation and cloning of DNA fragments, and plasmid transformations were by standard techniques as described in Molecular Cloning: A Laboratory Manual, Second Edition (1989), by Sambrook et al., Cold Spring Harbor Laboratory Press, Cold Spring Harbor, N.Y., USA.

7. The galactose-sensitive phenotype was screened on minimal A medium supplemented with Casamino acids and 0.2% galactose. The lactose-sensitive phenotype was screened on minimal A medium supplemented with Casamino acids, IPTG and 0.1%lactose.

Example 1

Obtaining a Kan(Ts) Mutation

A preparation of P1 phage grown on strain GJ523, which carries the zbh-900::Tn10dKan insertion 50% cotransducible with the galETK operon at 17 min was mutagenized in vitro with hydroxylamine as described [Cunningham-Rundles and Maas (1975) J. Bacteriol. 124:791–799]. The mutagenized phage stock was then used to transduce strain GJ1000 to Kan-resistance at 30° C. A collection of approximately 2000 Kan-resistant transductants was then replica-plated on pairs of Kan-supplemented plates, with one member of the pair being incubated at 30° C. and the other at 42° C. Fourteen mutants that putatively carried temperature-sensitive Kan-resistance mutations [Kan(Ts)] were identified as colonies that grew on Kan-containing plates at 30° C. but not at 42° C. One such mutant was designated GJ1112 and was inferred to carry a mutation that results in an altered neomycin phosphotransferase enzyme which has not been rendered temperature-sensitive for its catalytic activity. The corresponding allele was designated zbh-900:Tn10dKan (Ts)1.

Example 2

Determining the Frequency of lacZ::Kan Excision in Living and Essentially Nondividing Cells:

Strain GJ1823 was constructed from MG1655 in two successive steps of P1 transduction. The first involved the transfer into MG1655 of the Kan(Ts) mutation from GJ1112, which was effected by selection for Kan-resistance at 30° C. One such transductant which was shown to exhibit a temperature-sensitive Kan-resistance phenotype was then used as recipient for a cross with a P1 lysate grown on GJ513 (which carries the lacZ4525::Tn10dKan insertion in the lacZ gene) and the selection was for Kan-resistant transductants at 42° C. The resultant Lac-strain was designated GJ1823.

Another strain GJ1885 carrying both the zbh-900:Tn10dKan(Ts)1 and lacZ4525:Tn10dKan insertions was constructed in three sequential steps as follows. (i) Strain CSH142 was transduced to Kan-resistance at 30° C. with a P1 lysate grown on GJ1112. (ii) The resultant strain was used as recipient in conjugation with the Hfr donor KL226 and selection was made for Pro+ exconjugants at 30° C., with Kan-resistance as contraselection against the donor strain. An exconjugant that had also become Lac+ was chosen for the third step. (iii) In the third step, lacZ4525::Tn10dKan was introduced by P1 transduction from GJ513, with selection for Kan-resistance at 42° C. and then screening for the lacphenotype.

The frequencies of precise excision of the lacZ4525::Tn10dKan insertion in living and essentially non-dividing cells of strains GJ11823 and GJ11885 were determined by a Lac+ papillation assay modified from that described previously [Nghiem et al. (1988) Proc. Natl. Acad. Sci. USA 85:2709–2713; Reddy and Gowrishankar (1997) J. Bacteriol. 179:2892–2899]. Cultures of the strains were spread at dilutions sufficient to give approximately 25 colonies per plate (of 85 mm diameter) on LB agar medium supplemented with Kan, Xgal and 0.1% lactose. The plates were incubated for two to three days at 42° C. (the restrictive temperature for growth of the papillae arising out of the precise excision) following which the plates were shifted for incubation at 30° C. for five to seven days (the permissive condition). Lac+ papillae were visualized as blue-colored outgrowths on the surface of the colonies. The colonies were photographed. It has been shown that the central zone (two-thirds diameter) of each colony grown under such conditions represents cells that have remained essentially nondividing after shift to the permissive incubation temperature of 30° C. [Pirt (1967)J. Gen. Microbiol. 47:181–197; Cooper et al. (1968) Proc. R. Soc. Lond. B 171:175–199; Wimpenny (1979) J. Gen. Microbial. 114:483–486; Reddy and Gowrishankar (1997) Genetics 147:991–1001]. Therefore the numbers of Lac+ papillae in the said central zone of each of these colonies was determined from the photographs. These numbers were taken to represent the frequency of the precise excision of lacZ4525:Tn10dKan in living and essentially nondividing cells. The effect of mutation in each of the genes such as ssb, uup or mutS on the frequency of precise excision of lacZ4525:Tn10dKan in living and essentially nondividing cells was also determined in the appropriate mutant derivatives of GJ1823 or GJ1885 that were constructed by P1 transduction. The effect of substances such as caffeine at 0.5 mg per ml and 1 mg per ml on the said frequency was also determined by performing the assays in the presence of the said concentrations of the substance added to the agar medium.

It may be noted that procedures essentially similar to those of example 2 may be applied, with appropriate modifications that are familiar to the skilled artisan, also to the following additional instances of determination of mutation frequencies in living and essentially nondividing cells:

(i) Nearly precise excisions [defined in Foster et al. (1981) Cell 23:215–227] OF LACz4525:Tn10DKan, which would not reconstitute a functional lacZ gene but would relieve polarity on expression of the downstream lacY gene. This frequency may be monitored by a Lac$^+$ papillation assay on derivatives of GJ1823 or GJ1885 that carry the lacZ$^+$ but not the lacY gene on the extrachromosomal element such as an F-prime.

(ii) Excisions of other Kan-resistance insertions in lacZ (iii) Excisions of Kan-resistance insertions in other sugar-fermentation genes or operons in *Esherichia coli*.

It may be further noted that the gene encoding Kan-resistance in *Escherichia coli* also confers resistance to other aminoglycoside antibiotics such as neomycin in bacteria and G418 in Eukaryotic cells [Jimenez and Davies (1980) Nature 287:869–871; Webster and Dickson (1983) Gene 26:243–252.]

Example 3
Obtaining a galE(Ts) Mutation:

A P1 lysate prepared on strain GJ1112 was used to transduce strain PL2 to Kan-resistance at 30° C., and Kan-resistant transductants were identified that still retained the galactose-sensitive phenotype conferred by the galE28 mutation of the recipient. A P1 lysate prepared on one such transductant was then used to transduce strain CSH143 to Kan-resistance at 30° C., and the resulting transductants were screened for those that had co-inherited the galE28 mutation conferring the Galand galactose-sensitive phenotype. One such colony was designated GJ2202.

Spontaneous Gal+ mutants of strain GJ2202 were selected at 30° C. and the mutants were screened for a Galand galactose-sensitive phenotype at 43° C. A putative temperature-sensitive galE+ pseudorevertant [designated galE516(Ts)] that was so identified was designated GJ2203.

On Lac+ papillation medium (constituted of minimal A agar plates supplemented with casamino acids and 0.1% lactose) at 30° C., colonies of strain GJ2203 (which is a lacZ amber mutant) exhibited very small papillae, presumably because the galE(Ts) allele was not sufficiently Gal+ at the permissive temperature to allow rapid growth of the papillae. To overcome this problem, the galE516(Ts) mutation was transferred on to a multicopy plasmid as follows. Plasmid pAA102 [which is a pBR322 conferring Amp-resistance and derivative carrying the wild-type galETK operon and has a unique BstEII site toward the 5' end of galE and two EcoRV sites located respectively toward the 3' end of galE and in galT; Busby et al. (1982) J. Mol. Biol. 154:197–209] was first digested completely with BstEII and partially with EcoRV; the former end was "blunted" with Klenow DNA polymerase and the molecule was recircularized; this resulted in the deletion of a 1.1-kilobase BstEII-EcoRV segment internal to the galE gene, and the resultant ΔgakET+K+ plasmid was designated pHYD601. In the second step, a phage P1lysate prepared on a GJ2203/pHYD601 transformant was used to transduce GJ2202 simultaneously to Amp-resistance and Gal+ at 30° C., so as to identify plasmid derivatives into which the galE516(Ts) mutation had been transferred by homologous recombination from the chromosome of GJ2203. One such plasmid was designated pHYD603. GJ2203/pHYD603 derivatives exhibited satisfactory Lac+ papillation at 30° C. and continued to be Galand galactose-sensitive at 43° C.

Example 4
Determining the Frequency of Reversion of Lacto Lac+ in Living and Essentially Nondividing Cells:

Strain GJ2219 was constructed from strain CSH142 in four steps as follows: (i) A P1 lysate prepared on GJ2203 was used to transduce CSH142 to Kan-resistance at 30° C., and transductants that had co-inherited the galE51g(Ts) mutation were identified as ones that had become Galand galactose-sensitive at 43° C. (ii) A spontaneous galP mutant of one such transductant was then obtained by selection for resistance to 1 mM 2-deoxygalactose [Nagelkerke and Postma (1978) J. Bacteriol. 133:607–613]. (iii) The said galP mutant was then subjected to a selection for spontaneous mutants that would grow at 43° C. on minimal A medium supplemented with Casamino acids and 0.01% D-galactose. Two classes of galactose-resistant mutants were expected in this step: those with mutations in mgl (the desired category) and others with mutations in the galETK locus. The two categories were distinguished after making the strains Lac+ in the subsequent step. (iv) Several individual mutants from the preceding step were each used as recipients in conjugation with Hfr donor KL226, and selection was made for Pro+ exconjugants at 30° C., with Kan-resistance as contraselection against the donor strain. From one such cross, strain GJ2219 was identified as a colony that was able to grow on minimal A medium supplemented with lactose (at 0.1%), IPTG and Casamino acids at 30° but not at 43° C. [because of galE(Ts)-mediated killing at 43° C. after the hydrolysis of lactose to generate galactose]. The particular Fparent that had been used as recipient in the mating from which GJ2219 was identified was also saved, and was designated GJ2218.

Individual derivatives of strain GJ2219 each carrying a different chromosomal lacZ mutation were constructed by phage P1 transductions. For example, a lacZ4525:Tn10dKan derivative of GJ2219 was constructed with the use of a P1 phase lysate prepared on GJ513, with selection for Kan-resistant transductants at 42° C. and scoring for Laccolonies (at 30° C.). One such colony was designated GJ2220. In another example, a lacZ (Amber) mutation was introduced into GJ2219 in three steps as follows. In the first step, a P1 lysate prepared on strain CAg18420 was used to transduce MG1655 to Kan-resistance, and transductants were identified that had still retained the recipient lacZ+ gene. In the second step, a P1 lysate prepared one such Kan-resistant lacZ+ transductant was used to transduce strain CSH143 to Kan-resistance, and transductants were identified that had still retained the recipient lacZ (Amber) mutation. A P1 lysate prepared on one such Kan-resistant lacZ (Amber) transductant was then used in the third step to transduce GJ2219 to Kan-resistance at 40° C., and the resulting colonies were screened for ones that had become Lac–(at 30° C.) because of cotransduction of the LacZ (Amber) allele. One such colony was designated GJ2231. Each of the strains GJ2220 and GJ2231 was then transformed with plasmid pHYD603, with selection for Amp-resistance at 30° C.

Culture suspensions of the pHYD603 transformants of GJ2220 and GJ2231 were spotted, in 3-$\mu$l volumes that each contained approximately $10^4$ to $10^5$ cells, on the surface of Lac+-papillation agar plates of the following composition; minimal A supplemented with Amp, Casamino acids and 0.1% lactose. The density of spotting was such as not to exceed 20 per plate of 85-mm diameter. The plates were incubated at 43° C. for two to three days (restrictive temperature for Lac+) following which the plates were shifted to 30° C. (permissive conditions) and incubated at that temperature for five to seven days. Lac+ papillae that had grown on each spot were visualized by the gentle addition of 20 microlitres of Xgal solution (0.5 mg per ml) followed (once sufficient blue coloration had developed) by 20 microlitres of aqueous 1 M sodium carbonate. The spotted colonies were photographed and the numbers of Lac+ papillae in the central zone (two-thirds diameter) of each was determined. These numbers were taken to represent the frequency of reversion from Lac– to Lac+ in living and essentially non-dividing cells of the corresponding strains. The effect of mutation in each of the genes such as mutS, recA or mutY on the frequency of such reversion to Lac+ in living and essentially nondividing cells was also determined in the appropriate mutant derivatives of GJ220/pHYD603 or GJ2231/pHYD603 that were constructed by P1 transduction.

It may be noted that procedures essentially similar to those of example 4 may be applied, with appropriate modifications that are familiar to the skilled artisan, also to the following additional instances of determination of mutation frequencies in living and essentially nondividing cells.

(i) Reversion to Lac⁺ of other mutations in lac that confer a Lac⁻ phenotype Derivative of GJ2219/pHYD603 carrying such mutations on the chromosome may be constructed for the purpose by P1 transduction.

(ii) Reversion to Lac⁺ of mutations in lac that are carried on extrachromosomal elements such as F128 (that is, F-lac pro). Derivatives of strain GJ2218/pHYD603 carrying such extrachromosomal elements may be constructed and employed for the purpose.

Example 5
Performing a lacI Forward Mutation Assay in Living and Essentially Nondividing Cells:

The construction of strain GJ2406/pHYD603 from strain GJ2219 entailed the following steps: (i) Strain MG1655 was infected with lambda phage NK1324, and random transpositions of TN10dCm form NK1324 into the chromosome of MG1655 were obtained. (ii) A P1 lysate prepared on the pool of MG1655 Cm-resistant derivatives was used to transduce CSH143, and a double selection was imposed for Lac⁺ Cm-resistant transductants. In this manner, one colony was obtained in which the Tn10dCm insertion was linked (as determined by subsequent test transductional crosses) to the lac locus on the F-prime. The said Tn10dCm insertion was designated zah-910::TN10dCm. (iii) The zah-910::Tn10dCM insertion obtained in the preceding step was then transferred by P1 transduction into strain NR3835, and Cm-resistant colonies that had retained the lacI$^q$lacPL8 genotype of the recipient were identified as white colonies on LB-Xgal agar plates not supplemented with IPTG (as distinguished from those CM-resistant transductants in the same cross that had co-inherited the lac⁺ locus of the donor, which were pale blue on the plates). The former class of transductants (that is, lacI$^q$ lacPL8) were, as expected, darker blue on BL-Xgal agar plates that had been supplemented with IPTG than in the absence of such IPTG supplementation. (iv) A P1 lysate prepared on zah-910::Tn10dCm lacI$^q$ lacPL8 transductant obtained in the preceding step was used to transduce strain GJ2219 to Cm-resistance at 30° C. Transductants that had co-inherited the lacI$^q$ lacPL8 mutations were distinguished from these that had retained the recipient lac⁺ genotype by the same plate tests described in step iii, with the modification that the tests were done at 30° C. One such lacI$^q$ lacPL8 derivative was designated GJ2406. (iv) Plasmid pHYD603 was then introduced into strain GJ2406 by transformation, with selection for Amp-resistance at 30° C.

A culture of strain GJ2406/pHYD603 was grown at 30° C. to stationary phase in LB medium supplemented with 0.2% glucose and Amp. A 0.05-ml volume of a 1:10 dilution (in minimal A buffer) of the culture was overlaid in 1 ml of soft agar on a 35-mm agar plate of 0.05% glucose-0.2% Casamino acids-minimal A-Amp. The plate was incubated for 36 hours at 30° C., by which time the stain had grown up as a lawn on the plate. PG and Xgal were then added in a second 1-ml overlay of soft agar in such amount that their final concentrations (after diffusion through the whole volume of agar medium) would be 0.05% and 40 micrograms per ml respectively. The plate was immediately shifted to 43° C. and incubated at that temperature for three days (the restrictive condition for lacI mutants), and then shifted back to 30° C. (the permissive condition for lacI mutant papillae) for further incubation for 7 to 14 days. Papillae of lacI mutants were visualized as blue-colored outgrowths on the surface of the lawn. The number of papillae on the plate was counted, and this number was taken to represent the frequency of lacI forward mutation in living and essentially nondividing cells.

It may be noted that procedures essentially similar to those of example 5 may be applied, with appropriate modifications that are familiar to the skilled artisan, also to other configurations of a lacI forward mutation assay, including those in which the lac operon is carried on an extrachromosomal element such as F128. Derivatives of strain GJ2218/pHYD603 carrying such extrachromosomal elements may be constructed and employed for the purpose. The lacI$^q$ lacPL8 mutations are also present in strain CSH100.

Strains substantially genetically equivalent to GJ1823 or GJ1885 of example 2, GJ2220/pHYD603 and GJ2231/pHYD603 of example 4, and GJ2406/pHYD603 of example 5, may also be constructed by the skilled artisan from the deposited strains of this invention namely GJ2219 and GJ2251/pHYD603, with the use of resources available in the art. Such strain constructions have indeed also been achieved in this invention. Thus, plasmid pHYD603 DNA was prepared from GJ2251/pHYD603 for use in transformation experiments. Strain GJ2251/pHYD603 was cured of its plasmid spontaneously by culturing in LB medium in the absence of Amp and screening for Amp-sensitive colonies, and a P1 lysate prepared on one such plasmid-cured derivative (that is, GJ2251) was used as a source for transferrin the lacI$^q$ lacPL8 mutations in linkage with zah-910::Tn10dKan (Ts)I insertion by selection for Kan-resistance at 30° C. and scoring for retention of the Gal⁺ phenotype of the recipient by testing on galactose-minimal A at 43° C. The resulting transductant was then infected with the P1 lysate prepared on GJ2251 for transfer of the lacZ4525::Tn10dKan mutation, with selection for Kan-resistance at 42° C. (to construct the equivalent of stain GJ1823). Likewise, strain GJ2253 (whose genotype is identical to that of strain GJ2220) was constructed by infection of GJ2219 with P1 (GJ22510 and selection for Kan-resistance at 42° C. The galE516(ts) mutation was also transferred into other *Escherichia coli* strains with the use of the P1 lysate prepared on GJ2219 and selection for Kan-resistance at 30° C. followed by screening for the Gal and galactose-sensitive phenotypes at 43° C.

It may be also noted that the examples described may be easily adapted by a person skilled in the art for determining the effects of particular compounds or particular genes on the frequency of mutations in living and essentially nondividing cells.

What is claimed is:

1. A method for determining the frequency with which at least one target mutation arises in a population of living and non dividing cells, the method comprising:

(a) subjecting a cell population comprising indicator DNA, which produces a detectable phenotype, when mutated, to growth conditions, wherein the growth conditions are mutant-lethal resulting in a cell population free of cells with the target mutation;

(b) subjecting said resulting cell population to resting conditions which induce a cell cycle stationary phase;

(c) shifting said resulting cell population from mutant-lethal condition to a mutant-tolerant condition under which mutants reatain viability; and (d) detecting the phenotype in said viable mutant cells.

2. The method of claim 1, in which the growing cell population comprises conditionally-lethal DNA.

3. The method of claim 1 in which a potential mutagen is introduced at one or more of steps a.–c.

4. The method of claim 1 wherein the cells are bacterial cells.

5. The method of claim 4 wherein the cells are of the bacterium *Escherichia coli*.

6. The method of claim 1 in which the indicator DNA is a DNA sequence which encodes a protein with a detectable activity or which when mutated encodes a protein with a detectable activity.

7. The method of claim 6 in which the indicator DNA encodes a protein which affects production, in response to a chemical substance of a second protein with a detectable activity, and which indicator DNA, when mutated, affects the production of the second protein such that the production of the second protein is rendered constitutive and is not affected by the chemical substance.

8. The method of claim 7 in which the second protein is β-gelactosidase.

9. The method of claim 7 in which the chemical is isopropyl β-thiogalactopyranoside.

10. The method of claim 6 in which the indicator DNA in a cell population is unable to express a detectable protein with a particular detectable activity, and, which, when mutated, results in expression of the protein with the detectable activity.

11. The method of claim 10 in which the protein is beta-galactosidase.

12. The method of claim 2 in which the mutant-lethal condition is incubation at a particular temperature and the mutant-tolerant condition is incubation at a second particular temperature.

13. The method of claim 12 wherein the conditionally-lethal DNA is a temperature sensitive galE mutation.

14. The method of claim 12 wherein the conditionally-lethal DNA is a temperature sensitive kanamycin-resistance gene.

15. The method of claim 13 wherein the galE mutation is the galE516 allele present, for example, in *Escherichia coli* strains GJ2219 or GJ2406 or in plasmid pHYD603.

16. The method of claim 14 wherein the kanamycin-resistance gene is present, for example in *Escherichia coli* strains GJ1823 or GJ1885.

* * * * *